(12) United States Patent
Nagasawa et al.

(10) Patent No.: US 10,261,125 B2
(45) Date of Patent: Apr. 16, 2019

(54) SEMICONDUCTOR WAFER EVALUATION STANDARD SETTING METHOD, SEMICONDUCTOR WAFER EVALUATION METHOD, SEMICONDUCTOR WAFER MANUFACTURING PROCESS EVALUATION METHOD, AND SEMICONDUCTOR WAFER MANUFACTURING METHOD

(71) Applicant: SUMCO CORPORATION, Tokyo (JP)

(72) Inventors: Takahiro Nagasawa, Saga (JP); Keiichi Takanashi, Saga (JP)

(73) Assignee: SUMCO CORPORATION, Tokyo (JP)

(*) Notice: Subject to any disclaimer, the term of this patent is extended or adjusted under 35 U.S.C. 154(b) by 0 days.

(21) Appl. No.: 15/810,477

(22) Filed: Nov. 13, 2017

(65) Prior Publication Data
US 2018/0136279 A1    May 17, 2018

(30) Foreign Application Priority Data

Nov. 15, 2016 (JP) .................................. 2016-222479

(51) Int. Cl.
| | | |
|---|---|---|
| *G01R 31/317* | (2006.01) | |
| *H01L 21/66* | (2006.01) | |
| *G01R 31/3185* | (2006.01) | |
| *G01N 21/95* | (2006.01) | |

(52) U.S. Cl.
CPC ... *G01R 31/31711* (2013.01); *G01N 21/9501* (2013.01); *G01R 31/318511* (2013.01); *H01L 22/12* (2013.01); *H01L 22/20* (2013.01); *H01L 22/34* (2013.01); *H01L 2924/0002* (2013.01)

(58) Field of Classification Search
CPC ...... G01R 31/31711; G01R 31/318511; H01L 22/12; H01L 22/34; H01L 2924/0002; H01L 22/20; G01N 21/9501

USPC ............. 352/237.1–237.6, 239.1–239.8
See application file for complete search history.

(56) References Cited

U.S. PATENT DOCUMENTS

| | | | |
|---|---|---|---|
| 7,302,091 B2 | 11/2007 | Hamaguchi et al. | |
| 2004/0151362 A1 | 8/2004 | Hamaguchi et al. | |

FOREIGN PATENT DOCUMENTS

| | | |
|---|---|---|
| JP | H04-093837 | 3/1992 |
| JP | 2004-138563 | 5/2004 |
| JP | 2009-229218 | 10/2009 |
| JP | 2012-138493 | 7/2012 |

OTHER PUBLICATIONS

Japan Office Action, dated Jan. 9, 2018, issued in the corresponding Japanese Patent Application No. 2016-222479.

*Primary Examiner* — Tri T Ton
(74) *Attorney, Agent, or Firm* — Greenblum & Bernstein, P.L.C.

(57) ABSTRACT

The method of setting the evaluation standard of a semiconductor wafer includes setting the A and B on the basis of an abnormal substances overlooking rate "a" specific to the light-scattering type surface inspection apparatus specified by an apparatus-induced abnormal substances overlooking rate $\Phi$ due to the light-scattering type surface inspection apparatus and a probabilistic abnormal substances overlooking rate, in which A is the number of times of inspection, B is an abnormal substances detection threshold, the apparatus-induced abnormal substances overlooking rate $\Phi$ is higher as the target abnormal substances size to be detected is smaller, and the probabilistic abnormal substances overlooking rate is lower as the number of times of inspection increases.

9 Claims, No Drawings

SEMICONDUCTOR WAFER EVALUATION STANDARD SETTING METHOD, SEMICONDUCTOR WAFER EVALUATION METHOD, SEMICONDUCTOR WAFER MANUFACTURING PROCESS EVALUATION METHOD, AND SEMICONDUCTOR WAFER MANUFACTURING METHOD

CROSS-REFERENCE TO RELATED APPLICATIONS

This application claims priority under 35 U.S.C 119 to Japanese Patent Application No. 2016-222479 filed on Nov. 15, 2016. The above application is hereby expressly incorporated by reference, in its entirety.

BACKGROUND OF THE INVENTION

Field of the Invention

The present invention relates to a semiconductor wafer evaluation standard setting method, a semiconductor wafer evaluation method, a semiconductor wafer manufacturing process evaluation method, and a semiconductor wafer manufacturing method.

Discussion of the Background

As the method for evaluating various types of abnormal substances present on the surface of a semiconductor wafer, there is known a method for detecting the abnormal substances as a light point defect through the use of a light-scattering type surface inspection apparatus (for example, see Japanese Unexamined Patent Publication (KOKAI) No. 2012-138493, which is expressly incorporated herein by reference in its entirety).

SUMMARY OF THE INVENTION

The light-scattering type surface inspection apparatus irradiates, with light, the surface of a sample to be evaluated, and detects the abnormal substance present on the surface of the sample to be evaluated, as a light point defect, on the basis of the scattered light from this surface, and is referred to also as a laser surface-inspection apparatus, a surface inspection apparatus, a surface inspection machine, or the like.

Examples of the abnormal substances present on the surface of a semiconductor wafer include a surface local abnormal shape (defect) and a surface deposit which is referred to as a particle. The presence of such abnormal substances on the surface of a semiconductor wafer to be used as a semiconductor substrate may cause a degradation of device characteristics. Therefore, in the field of manufacturing semiconductor wafers, the presence state of abnormal substances on the surface of a semiconductor wafer is evaluated, and on the basis of this evaluation result, a semiconductor wafer manufacturing process is managed so as to suppress the introduction and/or adhesion of the abnormal substances onto the surface. In addition, lot sampling inspection is also performed, a sampled semiconductor wafer is evaluated, and a semiconductor wafer of the same lot as a semiconductor wafer determined as an acceptable level of an evaluation item concerning the presence state of abnormal substances is shipped as an acceptable product wafer. Furthermore, a manufactured semiconductor wafer is also inspected, and a semiconductor wafer determined as an acceptable level of an evaluation item concerning the presence state of abnormal substances is shipped as an acceptable product wafer.

If the abnormal substances on the surface of a semiconductor wafer can be more sensitively detected in such evaluation, a high-quality semiconductor wafer can be stably supplied in which the introduction and/or adhesion of abnormal substances onto the surface are suppressed.

An aspect of the present invention provides for a novel method capable of sensitively evaluating the abnormal substances present on the surface of a semiconductor wafer through the use of a light-scattering type surface inspection apparatus.

An aspect of the present invention relates to:

a method of setting the evaluation standard of a semiconductor wafer (hereinafter, referred to also as an "evaluation standard setting method"), wherein the evaluation standard is a standard that is used in evaluating a semiconductor wafer by a light-scattering type surface inspection apparatus which detects the abnormal substances present on the surface of the semiconductor wafer as a light point defect;

the light-scattering type surface inspection apparatus includes an analysis unit which outputs, as abnormal substances data, only the data of abnormal substances detected as the abnormal substances having a size equal to or greater than X;

setting the evaluation standard is setting the number of times of inspection A and an abnormal substances detection threshold B, in which the A and B are the values to be used in the evaluation of determining a light point defect, at which abnormal substances data is output B or more times within A-times of inspection, as a light point defect brought by abnormal substances, where A is an integer equal to or greater than 2, and B is an integer equal to or greater than 1 and equal to or less than A; and the method includes setting the A and B on the basis of an abnormal substances overlooking rate "a" specific to the light-scattering type surface inspection apparatus specified by an apparatus-induced abnormal substances overlooking rate Φ due to the light-scattering type surface inspection apparatus and a probabilistic abnormal substances overlooking rate, in which the apparatus-induced abnormal substances overlooking rate Φ is higher as the target abnormal substances size to be detected is smaller, and the probabilistic abnormal substances overlooking rate is lower as the number of times of inspection increases.

A light-scattering type surface inspection apparatus irradiates, with light, the surface of a semiconductor wafer to be evaluated, and detects the scattered light from a light point defect on the surface of the wafer to recognize the size and position of the abnormal substances. However, the light point defects detected by the light-scattering type surface inspection apparatus may include not only a light point defect due to abnormal substances but also noise. For such noise, Japanese Unexamined Patent Publication (KOKAI) No. 2012-138493 proposes that, under a detection condition that the number of light point defects (LPD; Light Point Defects) detected in one time of inspection of a wafer by a light-scattering type surface inspection apparatus is equal to or less than a reference value, a light point defect detected twice or more at the same position is regarded as a light point defect which is not affected by noise but caused by a defect (see claim 1, paragraph 0008, and the like of Japanese Unexamined Patent Publication (KOKAI) No. 2012-138493). However, the present inventors conceive that, in such evaluation standard, an apparatus-induced factor due to a light-scattering type surface inspection apparatus and a probabilistic factor are not sufficiently taken into consideration. In contrast, in the evaluation standard setting method which the present inventors have newly found, evaluation standard are set for determining whether or not a light point defect detected by a light-scattering type surface inspection apparatus is a light point defect brought by abnormal substances, on the basis of an apparatus-induced abnormal substances overlooking rate and an apparatus-specific abnormal substances overlooking rate specified by a probabilistic abnormal substances overlooking rate. The present inventors conceive that, by evaluating a semiconductor wafer based on the evaluation standard set in such a manner, the abnormal substances present on the surface of the semiconductor wafer can be more sensitively detected. The above evaluation standard setting method will be described in detail below.

In the present invention and specification, the term "abnormal substances" is used so as to mean to include a local abnormal shape (i.e., defect) on the surface of a semiconductor wafer and an alien substance adhering to the surface of a semiconductor wafer (surface deposit). A specific embodiment of abnormal substances will be described later.

In an embodiment, the apparatus-induced abnormal substances overlooking rate Φ is the probability for the light-scattering type surface inspection apparatus not to output, as abnormal substances data, the data of abnormal substances having a size "m" present on the surface of a semiconductor wafer to be evaluated, in the analysis unit, and is obtained by Relational Expression 1 below, and the apparatus-specific abnormal substances overlooking rate "a" is obtained by Relational Expression 2 below.

(Relational Expression 1)

$$\phi(z) = \frac{1}{\sqrt{2\pi}} e^{-\frac{z^2}{2}}$$

$$\Phi(z) = \int_{-\infty}^{z} \phi(y) dy$$

[In Relational Expression 1, Z=(X−m)/σ, and σ is the standard deviation of the variation in detection size due to the light-scattering type surface inspection apparatus.]

$$a = P(k) + P(k+1) + \ldots + P(n) \quad \text{(Relational Expression 2)}$$

[In Relational Expression 2, P is the probability for the abnormal substances present on the surface of a semiconductor wafer to be probabilistically overlooked k-times without being detected in n-times of inspection, where k≤n, and is calculated by a binomial distribution below.]

$$P[X = k] = \binom{n}{k} \Phi^k (1-\Phi)^{n-k} \text{ for } k = 0, 1, 2, \ldots, n$$

$$\binom{n}{k} = {}_nC_k = \frac{n!}{k!(n-k)!}$$

In an embodiment, the above evaluation standard setting method includes setting a target abnormal substances overlooking rate; and setting the A and B to values such that the overlooking rate calculated from the A and B is equal to or lower than the target abnormal substances overlooking rate.

In an embodiment, the target abnormal substances overlooking rate is set to a lower value as the quality requested for a semiconductor wafer to be evaluated is higher.

A further aspect of the present invention relates to a semiconductor wafer evaluation method, the method including: setting evaluation standard by the above evaluation standard setting method; and evaluating a semiconductor wafer based on the evaluation standard that has been set.

A still further aspect of the present invention relates to a semiconductor wafer manufacturing process evaluation method, the method including: evaluating, by the above semiconductor wafer evaluation method, a semiconductor wafer manufactured in a semiconductor wafer manufacturing process to be evaluated; and determining, on the basis of a result of the evaluation, the necessity of a process control of the semiconductor wafer manufacturing process to be evaluated.

A still further aspect of the present invention relates to a semiconductor wafer manufacturing method, the method including: manufacturing a semiconductor wafer in a semiconductor wafer manufacturing process; evaluating at least one semiconductor wafer manufactured in the above semiconductor wafer manufacturing process by the semiconductor wafer evaluation method; determining, on the basis of a result of the evaluation, the necessity of a process control of the semiconductor wafer manufacturing process; and, when it is determined, as a result of the determination, that the process control is not required, then further manufacturing a semiconductor wafer in the semiconductor wafer manufacturing process without the process control, while when it is determined, as a result of the determination, that the process control is required, then further manufacturing a semiconductor wafer in the semiconductor wafer manufacturing process after performing the process control of the semiconductor wafer manufacturing process.

A still further aspect of the present invention relates to a semiconductor wafer manufacturing method, the method including: preparing a semiconductor wafer lot including a plurality of semiconductor wafers; extracting at least one semiconductor wafer from the lot; evaluating the extracted semiconductor wafer; and subjecting at least one semiconductor wafer included in the same lot as a semiconductor wafer which has been determined as an acceptable wafer by the evaluation, to preparation for shipping as a product semiconductor wafer, wherein the evaluation of the extracted semiconductor wafer is performed by the above semiconductor wafer evaluation method.

A still further aspect of the present invention relates to a semiconductor wafer manufacturing method, the method including: manufacturing a semiconductor wafer in a semiconductor wafer manufacturing process; evaluating a manufactured semiconductor wafer; and subjecting a semiconductor wafer which has been determined as an acceptable wafer by the evaluation, to preparation for shipping as a product semiconductor wafer, wherein the evaluation is performed by the above semiconductor wafer evaluation method.

According to an aspect of the present invention, abnormal substances present on the surface of a semiconductor wafer can be sensitively evaluated through the use of a light-scattering type surface inspection apparatus. Moreover, accordingly, a high-quality semiconductor wafer can be stably supplied in which the introduction and/or adhesion of abnormal substances onto the surface of the wafer are suppressed.

Other exemplary embodiments and advantages of the present invention may be ascertained by reviewing the present disclosure.

DETAILED DESCRIPTION OF THE EMBODIMENTS

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

Except where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not to be considered as an attempt to limit the application of the doctrine of equivalents to the scope of the claims, each numerical parameter should be construed in light of the number of significant digits and ordinary rounding conventions.

Additionally, the recitation of numerical ranges within this specification is considered to be a disclosure of all numerical values and ranges within that range. For example, if a range is from about 1 to about 50, it is deemed to include, for example, 1, 7, 34, 46.1, 23.7, or any other value or range within the range.

The following preferred specific embodiments are, therefore, to be construed as merely illustrative, and non-limiting to the remainder of the disclosure in any way whatsoever. In this regard, no attempt is made to show structural details of the present invention in more detail than is necessary for fundamental understanding of the present invention; the description taken with the drawings making apparent to those skilled in the art how several forms of the present invention may be embodied in practice.

Semiconductor Wafer Evaluation Standard Setting Method

An aspect of the present invention relates to:

a method of setting the evaluation standard of a semiconductor wafer, wherein the evaluation standard is a standard that is used in evaluating a semiconductor wafer by a light-scattering type surface inspection apparatus which detects the abnormal substances present on the surface of the semiconductor wafer as a light point defect;

the light-scattering type surface inspection apparatus includes an analysis unit which outputs, as abnormal substances data, only the data of abnormal substances detected as the abnormal substances having a size equal to or greater than X;

setting the evaluation standard is setting the number of times of inspection A and an abnormal substances detection threshold B, in which the A and B are the values to be used in the evaluation of determining a light point defect, at which abnormal substances data is output B or more times within A-times of inspection, as a light point defect brought by abnormal substances, where A is an integer equal to or greater than 2, and B is an integer equal to or greater than 1 and equal to or less than A; and the method includes setting the A and B on the basis of an abnormal substances overlooking rate "a" specific to the light-scattering type surface inspection apparatus specified by an apparatus-induced abnormal substances overlooking rate Φ due to the light-scattering type surface inspection apparatus and a probabilistic abnormal substances overlooking rate, in which the apparatus-induced abnormal substances overlooking rate Φ is higher as the target abnormal substances size to be detected is smaller, and the probabilistic abnormal substances overlooking rate is lower as the number of times of inspection increases.

Hereinafter, the above evaluation standard setting method will be explained further in detail.

<Semiconductor Wafer, Abnormal Substances>

A semiconductor wafer to be evaluated on the basis of the evaluation standard set by the above evaluation standard setting method can be various types of semiconductor wafers generally used as a semiconductor substrate. For example, the specific examples of the semiconductor wafer can include various types of silicon wafers. A silicon wafer can be, for example, a silicon single crystal wafer having passed through various kinds of processing processes after being cut out from a silicon single crystal ingot, for example, a polished wafer having been subjected to polishing and having a polished surface on the surface thereof. In addition, the silicon wafer can be various types of silicon wafers, such as an epitaxial wafer having an epitaxial layer on a silicon single crystal wafer and an annealed wafer having a modifying layer which is formed by annealing a silicon single crystal wafer. Moreover, a silicon wafer to be evaluated can be of an n-type or a p-type. Moreover, the dopant concentration (i.e., resistivity), oxygen concentration thereof, and the like are not to be limited. The diameter of the surface of a silicon wafer to be evaluated can be 200 mm, 300 mm, or 450 mm, for example, but not particularly limited thereto.

Examples of the abnormal substances which may be present on the surface of a semiconductor wafer include a surface local abnormal shape (defect) and a surface deposit, as described above. Examples of the defect include various types of shapes of defects, such as a concave defect and a convex defect. For example, the concave defect is the so-called groove. On the other hand, the convex defect is a local rising (projection) of a part of the surface. Such a surface local abnormal shape is usually introduced onto the surface of a semiconductor wafer by mechanical or chemical processing. As an example, a polished wafer is usually manufactured sequentially through the steps of rough polishing, etching, mirror polishing (finish polishing), and the like and has a polished surface (mirror surface) on the surface thereof. A defect may be introduced onto the polished surface due to the processing processes, such as polishing. Examples of such a defect include a linear defect. The linear defect refers to a linear concave or convex defect, but the shape in a plan view does not necessarily need to be a perfect line. For example, a linear concave defect present on the polished surface of a polished wafer is generally referred to as a scratch, and is usually introduced by polishing. On the other hand, a linear convex defect is referred to as a PID (Polished Induced Defect). The PID is usually introduced onto the polished surface of a polished wafer by polishing, such as the mirror polishing or the rough polishing (for example, lapping) usually performed before mirror polishing. As explained above, in an embodiment, the defect is the processing-induced defect which is introduced onto the surface of a silicon wafer in the processing step performed in the semiconductor wafer manufacturing process.

On the other hand, another aspect of the abnormal substances is a surface deposit, and is usually referred to as a particle.

\<Light-Scattering Type Surface Inspection Apparatus\>

As the light-scattering type surface inspection apparatus, a light-scattering type surface inspection apparatus having a known arrangement can be used without any limitation. The light-scattering type surface inspection apparatus usually scans, with a laser beam, the surface of a semiconductor wafer to be evaluated, detects, on the basis of scattered light, abnormal substances on the surface of the wafer as a light point defect, and recognizes the size and position of the abnormal substances by measuring the scattered light from the light point defect. Ultraviolet light, visible light, and the like can be used as the laser beam, and the wavelength thereof is not to be particularly limited. The ultraviolet light refers to the light having the wavelength region of less than 400 nm, while the visible light refers to the light having a wavelength region of 400 nm to 600 nm. The specific examples of a commercially available light-scattering type surface inspection apparatus can include Surfscan series SP1, SP2, SP3, and SP5 manufactured by KLA TENCOR Corporation. However, these apparatuses are exemplary only, and other light-scattering type surface inspection apparatuses can be also used.

An analysis unit of the light-scattering type surface inspection apparatus usually converts, on the basis of a correlation formula between the size of a reference particle and the size of a light point defect brought by the reference particle, the size of a light point defect detected by the light-scattering type surface inspection apparatus to an abnormal substances size. The analysis unit configured to perform such conversion usually includes a PC (Personal Computer) in which conversion software is mounted, and the arrangement of the analysis unit is known. However, if the analysis unit detects all the light point defects having different sizes as the abnormal substances, it becomes difficult to discriminate between noise and abnormal substances, and the sensitivity of detecting abnormal substances by the light-scattering type surface inspection apparatus will decrease. Then, usually in the analysis unit of the light-scattering type surface inspection apparatus, the minimum detection size is set, and only the data of abnormal substances having a size equal to or greater than the set size is output. A light-scattering type surface inspection apparatus used for the evaluation of a semiconductor wafer, in which evaluation standard are set by the above evaluation standard setting method, also includes the analysis unit. That is, the light-scattering type surface inspection apparatus outputs, as the data of abnormal substances, only the data of abnormal substances which is detected as abnormal substances having the size equal to or greater than X, where X represents the minimum detection size. In other words, when a size which is converted on the basis of the detected light-point-defect size is smaller than X, the analysis unit will determine that such a light point defect is not abnormal substances and will not output the data thereof as abnormal substances data. The sizes can refer to, for example, the diameter or maximum length of a surface deposit, the width or maximum length of a defect, and the like.

\<Setting of Evaluation Standard\>

Regarding the abnormal substances data output from the analysis unit, the present inventors have led to, through repeated intensive studies, focusing on the fact that, in the inspection by a light-scattering type surface inspection apparatus, even abnormal substances having an actual size equal to or greater than X may be recognized as abnormal substances having a size smaller than X and the abnormal substances data may not be output from the analysis unit due to the variation in detection size (including the influences from both the apparatus-induced variation in detection size and the probabilistic variations in detection size) specific to the light-scattering type surface inspection apparatus. That is, abnormal substances having an actual size equal to or greater than X have a certain variation in size due to a light-scattering type surface inspection apparatus, and thus the abnormal substances data may not be output from the analysis unit (i.e., may be overlooked). Furthermore, the smaller a target abnormal substances size to be detected, the more difficult the detection by a light-scattering type surface inspection apparatus tends to become, and therefore the probability for the overlooking of abnormal substances to occur due to an apparatus (apparatus-induced abnormal substances overlooking rate Φ) will increase as the target abnormal substances size to be detected is smaller. On the other hand, because, in terms of the probability theory, the detection accuracy will improve as the number of times of inspection by a light-scattering type surface inspection apparatus is increased, the probability for the overlooking of abnormal substances to probabilistically occur (the probabilistic overlooking rate of abnormal substances) will decrease as the number of times of inspection by a light-scattering type surface inspection apparatus is increased. When A-times of inspection are performed for the same semiconductor wafer, a light point defect at which abnormal substances data has been detected A times can be determined as the light point defect due to abnormal substances which is reliably present on the surface of a semiconductor wafer, but in view of the occurrence of overlooking of abnormal substances due to the above two factors, the light point defects at which abnormal substances data has been detected less than A times in A-times of inspection may include a light point defect due to abnormal substances which is probably present on the surface of a semiconductor wafer. In order to detect such a light point defect due to abnormal substances which is reliably present or which is probably present on the surface of a semiconductor wafer, "how many times inspection is to be performed?" and "among such number of times of inspection, whether or not a light point defect, at which at least how many times abnormal substances data has been output, is determined as the light point defect brought by abnormal substances", (i.e., evaluation standard), can be set based on the abnormal substances overlooking rate "a" specific to a light-scattering type surface inspection apparatus used for evaluation, in the evaluation standard setting method according to an aspect of the present invention. That is, in the above evaluation standard setting method, "A" and "B" which are the values used for the evaluation that a light point defect, at which A-times of inspection are performed and abnormal substances data are output B times or more times, can be determined as a "light point defect brought by abnormal substances" are set on the basis of the apparatus-specific abnormal substances overlooking rate "a". As described above, the overlooking of abnormal substances occurs due to an apparatus and also probabilistically occurs. Accordingly, the apparatus-specific abnormal substances overlooking rate "a" is specified by the apparatus-induced abnormal substances overlooking rate and the probabilistic abnormal substances overlooking rate. That is, by setting A and B on the basis of the apparatus-specific overlooking rate "a", evaluation standard can be set sufficiently taking into consideration the apparatus-induced factor and the probabilistic factor. The present inventors conceive that, by setting the evaluation standard sufficiently taking into consideration the apparatus-induced factor and the probabilistic factor, the detection sensitivity of abnormal substances present on the surface of a semiconductor wafer can be improved.

The number of times of inspection A set in the above evaluation standard setting method is an integer equal to or greater than 2, and the abnormal substances detection threshold B is an integer equal to or greater than 1 and equal to or less than A, preferably an integer equal to or greater than 1 and less than A. For example, A can be an integer of 2 to 100 and B can be an integer of 1 to 100, but A and B can be set on the basis of the apparatus-specific abnormal substances overlooking rate "a", and are not to be limited to the above-exemplified ranges.

Hereinafter, a specific embodiment will be described in which A and B are set on the basis of the apparatus-specific abnormal substances overlooking rate "a". However, the following specific embodiment is exemplary and the present invention is not to be limited to the exemplified embodiment.

(Specific Embodiment for Setting Evaluation Standard)

The apparatus-induced abnormal substances overlooking rate $\Phi$ can be determined by performing the performance evaluation for grasping the occurrence tendency of the overlooking of abnormal substances of a light-scattering type surface inspection apparatus which is actually used for evaluation of a semiconductor wafer. The performance evaluation can be conducted as follows, for example.

(A) Obtaining the variation in detection size output as a different size even if a measurement object having the same size is evaluated by a light-scattering type surface inspection apparatus which is actually used for evaluation of a semiconductor wafer. The measurement object for obtaining the variation in detection size may be the abnormal substances present on the surface of a semiconductor wafer, or may be a sample particle, such as a reference particle. The variation in detection size due to a light-scattering type surface inspection apparatus is obtained as a standard deviation $\sigma$.

(B) If the apparatus-induced abnormal substances overlooking rate $\Phi$ is defined as the probability for the light-scattering type surface inspection apparatus not to output, as abnormal substances data by the analysis unit, the data of abnormal substances having a size "m" present on the surface of a semiconductor wafer to be evaluated, then the apparatus-induced abnormal substances overlooking rate $\Phi$ can be obtained by Relational Expression 1 below.

$$\phi(z) = \frac{1}{\sqrt{2\pi}} e^{-\frac{z^2}{2}}$$

$$\Phi(z) = \int_{-\infty}^{z} \phi(y) dy$$

(Relational Expression 1)

[In Relational Expression 1, Z=(X−m)/σ, and σ is the standard deviation of the variation in detection size due to the light-scattering type surface inspection apparatus.]

On the other hand, the apparatus-specific abnormal substances overlooking rate can be obtained in accordance with the probability theory, specifically, by Relational Expression 2 below which includes the apparatus-induced abnormal substances overlooking rate $\Phi$ as an element.

$$a = P(k) + P(k+1) + \ldots + P(n)$$ (Relational Expression 2)

[In Relational Expression 2, P is the probability for the abnormal substances present on the surface of a semiconductor wafer to be probabilistically overlooked k-times without being detected in n-times of inspection, where k≤n, and is calculated by a binomial distribution below.]

$$P[X = k] = \binom{n}{k} \Phi^k (1-\Phi)^{n-k} \text{ for } k = 0, 1, 2, \ldots, n$$

$$\binom{n}{k} = {}_nC_k = \frac{n!}{k!(n-k)!}$$

Moreover, in an embodiment, it is also possible to set a target abnormal substances overlooking rate and set A and B to values such that the abnormal substances overlooking rate calculated from the A and B to become equal to or lower than the target abnormal substances overlooking rate. Since the abnormal substances present on the surface of a semiconductor wafer can be more reliably detected as the abnormal substances overlooking rate is lower, a semiconductor wafer can be more sensitively evaluated. Accordingly, as the quality requested for a semiconductor wafer to be evaluated is higher, the target overlooking rate is preferably set to a lower value so as to increase the evaluation sensitivity. Regarding the setting of the target abnormal substances overlooking rate, a specific embodiment will be described in Examples described later.

According to the above evaluation standard setting method, the evaluation standard used in evaluating a semiconductor wafer by a light-scattering type surface inspection apparatus can be set sufficiently taking into consideration the apparatus-induced factor and the probabilistic factor, so that the evaluation standard enabling high-sensitivity evaluation can be set.

Semiconductor Wafer Evaluation Method

A further aspect of the present invention relates to a semiconductor wafer evaluation method, the method including setting evaluation standard by the above evaluation standard setting method; and evaluating a semiconductor wafer based on the evaluation standard that has been set.

The evaluation standard setting method used in the above semiconductor wafer evaluation method is as described above in detail. In the above semiconductor wafer evaluation method, the presence state of abnormal substances on the surface of a semiconductor wafer to be evaluated can be evaluated by a light-scattering type surface inspection apparatus on the basis of the evaluation standard set in this manner. Examples of the evaluation items include various types of evaluation items usually used as the evaluation items of a semiconductor wafer, such as the number of abnormal substances whose data are detected, the abnormal substances size, and an in-plane distribution state of abnormal substances (for example, the presence or absence of a local abnormal distribution). Examples of the standard for determining the acceptable level/unacceptable level include the followings: (1) a threshold is set for the number of abnormal substances whose data is output from the analysis unit of the light-scattering type surface inspection apparatus, and if the number is equal to or less than the threshold, it is determined as an acceptable level having few abnormal substances; and (2) the in-plane distribution of abnormal substances is evaluated on the basis of the position coordinate of the abnormal substances output from the analysis unit of the light-scattering type surface inspection apparatus, and if an abnormal distribution is confirmed in which abnormal substances are locally dense on the surface of a semiconductor wafer, it is determined as an unacceptable level and/or if it is confirmed that abnormal substances are present at a specific position from which the presence of abnormal substances should be excluded, it is determined as an unacceptable level. The results of such evaluation can be used for the determination of the necessity of the process control of a semiconductor wafer manufacturing process, the determination of pass/fail of a sampling inspection, the determination of the pass/fail of 100% inspection, and the like etc. The details thereof will be described below.

Semiconductor Wafer Manufacturing Process Evaluation Method

A further aspect of the present invention relates to a semiconductor wafer manufacturing process evaluation method, the method including: evaluating, by the above evaluation method, a semiconductor wafer manufactured in a semiconductor wafer manufacturing process to be evaluated; and determining, on the basis of a result of the evaluation, the necessity of a process control of the semiconductor wafer manufacturing process to be evaluated.

Hereinafter, the semiconductor wafer manufacturing process evaluation method will be described in more detail.

Examples of the semiconductor wafer manufacturing process to be evaluated include a process for manufacturing various types of semiconductor wafers described above. For example, a polished wafer can be manufactured by a manufacturing process including: slicing a silicon wafer from a silicon single crystal ingot grown by a Czochralski method (CZ method) or the like; rough polishing (for example, lapping); etching; mirror polishing (finish polishing); and washing to be performed between the above processing steps or after the above processing steps. In addition, an annealed wafer can be manufactured by subjecting a polished wafer manufactured in the above manner to annealing. An epitaxial wafer can be manufactured by forming, by vapor-phase growth (epitaxial growth), an epitaxial layer on the surface of the polished wafer manufactured in the above manner. The necessity of process control of various types of semiconductor wafer manufacturing processes as descried above can be determined by the above semiconductor wafer manufacturing process evaluation method. The term "process control" means conducting at least the one selected from the group consisting of the replacement of a member, the repair of a member, the washing of a member, the replacement of a chemical liquid, a change of the semiconductor wafer processing condition, and a change of the washing condition. For example, the degradation of a member and/or a chemical liquid, the employment of an inappropriate processing condition, and the like may cause the introduction of a defect onto and/or the adhesion of a surface deposit to the surface of a semiconductor wafer which is manufactured in the semiconductor wafer manufacturing process. In contrast, by performing the process control as described above, the introduction/adhesion of abnormal substances onto the surface of a semiconductor wafer manufactured in the semiconductor wafer manufacturing process can be suppressed. However, it is not easy to determine the necessity of a process control without using any indicator and this is also inefficient. In contrast, in the above semiconductor wafer manufacturing process evaluation method, a semiconductor wafer manufactured in the semiconductor wafer manufacturing process to be evaluated is evaluated with the semiconductor wafer evaluation method according to an aspect of the present invention, and on the basis of the obtained result, the necessity of a process control of the semiconductor wafer manufacturing process to be evaluated is determined. That is, the necessity of the process control can be determined by using, as an indicator, the result obtained by the semiconductor wafer evaluation method according to an aspect of the present invention. The necessity of the process control can be determined, for example, on the basis of the standard regarding the acceptable level/unacceptable level of a semiconductor wafer described above. The standard, such as a threshold, for determining that the process control is required are not limited in particular, and can be set in accordance with the quality required for a product semiconductor wafer If it is determined, as a result of the evaluation, that the process control is required, then the process control of the semiconductor wafer manufacturing process is performed. The process control is as described above. As an example, when the process control of the polishing step is performed in the manufacturing process of a polished wafer, examples of the specific embodiment of the process control include the replacement of a polishing cloth, the replacement of a slurry containing polishing abrasive, a change of the polishing pressure, a change of the washing condition, and the like. For example, the degradation of a polishing cloth or slurry may cause the introduction of a defect onto the polished surface of a polished wafer. A defect may also be introduced onto the polished surface of a polished wafer if the polishing pressure is inadequate. Moreover, when washing is insufficient, a surface deposit (particle) may remain on the surface of a polished wafer without being removed by washing. If the various types of abnormal substances present on the polished surface of a polished wafer manufactured in the manufacturing process to be evaluated are evaluated on the basis of the semiconductor wafer evaluation method according to an aspect of the present invention, and the process control is performed on the basis of the obtained result (presence state of the abnormal substances on the polished surface), then after the process control, the introduction of a defect onto the polished surface of a polished wafer can be suppressed and/or the remaining of a surface deposit (particle) can be suppressed.

Semiconductor Wafer Manufacturing Method

A further aspect of the present invention relates to a semiconductor wafer manufacturing method (hereinafter, referred to as "Manufacturing Method"), the method including: manufacturing a semiconductor wafer in a semiconductor wafer manufacturing process; evaluating, by the above evaluation method, at least one semiconductor wafer manufactured in the semiconductor wafer manufacturing process; determining, on the basis of a result of the evaluation, necessity of a process control of the semiconductor wafer manufacturing process; and when it is determined, as a result of the determination, that the process control is not required, further manufacturing a semiconductor wafer in the semiconductor wafer manufacturing process without the process control, while when it is determined, as a result of the determination, that the process control is required, further manufacturing a semiconductor wafer in the semiconductor wafer manufacturing process after performing the process control of the semiconductor wafer manufacturing process.

Manufacturing Method 1 includes evaluating a silicon wafer manufacturing process by the semiconductor wafer manufacturing process evaluation method according to an aspect of the present invention described above; and performing a process control as required. The details of the evaluation and process control of the manufacturing process are as described above. By determining the necessity of a process control in the above manner and performing the process control as required, a high-quality semiconductor wafer can be stably supplied in which the introduction and/or adhesion of abnormal substances onto the surface can be suppressed. In the semiconductor wafer manufacturing process, manufacturing of a plurality of semiconductor wafers is usually performed continuously or intermittently. A semiconductor wafer to be subjected to evaluation may be one of a plurality of semiconductor wafers manufactured in the above manner, or the number of semiconductor wafers to be subjected to evaluation may be two or more and is not limited in particular.

An embodiment of Manufacturing Method 1 is a method of manufacturing a polished wafer, and the details thereof, such as the process control, are as described above. However, Manufacturing Method 1 is not limited to the method of manufacturing a polished wafer, and can be a method of manufacturing various types of semiconductor wafers, for example, those as described above.

A further aspect of the present invention relates to a semiconductor wafer manufacturing method (hereinafter, referred to as "Manufacturing Method 2"), the method including: preparing a semiconductor wafer lot including a plurality of semiconductor wafers; extracting at least one semiconductor wafer from the lot; evaluating the extracted semiconductor wafer; and subjecting at least one semiconductor wafer included in the same lot as a semiconductor wafer which has been determined as an acceptable wafer by the evaluation, to preparation for shipping as a product semiconductor wafer, wherein the evaluation of the extracted semiconductor wafer is performed by the above evaluation method.

Manufacturing Method 2 includes performing a lot sampling inspection; and evaluating a sampled semiconductor wafer by the semiconductor wafer evaluation method according to an aspect of the present invention. Then, if the sampled semiconductor wafer is determined as an acceptable wafer as a result of the evaluation, at least one semiconductor wafer included in the same lot as this semiconductor wafer is subjected to preparation for shipping as a product semiconductor wafer. On the other hand, if it is determined as an unacceptable wafer, then it is not shipped as a product or it is subjected to the preparation for shipping as a product semiconductor wafer after being subjected to a process for removing or reducing abnormal substances. Thus, a high-quality silicon wafer can be stably supplied in which the introduction and/or adhesion of the abnormal substances onto to the surface are suppressed. Examples of the preparation for shipping as a product semiconductor wafer include the washing prior to shipment, packing, and the like.

In Manufacturing Method 2, whether a sampled and evaluated semiconductor wafer is an acceptable wafer or an unacceptable wafer can be determined on the basis of the standard of the acceptable level/unacceptable level regarding a semiconductor wafer described above. The standard, such as a threshold, for determining as an unacceptable wafer are not limited in particular, and can be set in accordance with the quality required for a product semiconductor wafer. Further, the semiconductor wafers to be sampled may be one or more in a lot or may be two or more, and the number of the semiconductor wafers to be sampled is not limited in particular. Moreover, the sampled and evaluated semiconductor wafer can be subjected to the preparation for shipping as a product semiconductor wafer after the evaluation, or can also be subjected to the preparation for shipping as a product semiconductor wafer after being subjected to the process for removing or reducing abnormal substances.

An embodiment of Manufacturing Method 2 is a method of manufacturing a polished wafer, and the lot of semiconductor wafers can be the lot of polished wafers. The detail of the method of manufacturing a polished wafer is as described above. However, Manufacturing Method 2 is not limited to the method of manufacturing a polished wafer, and can be a method of manufacturing various types of semiconductor wafers, for example, those described above.

A further aspect of the present invention relates to a semiconductor wafer manufacturing method (hereinafter, referred to as "Manufacturing method 3"), the method including: manufacturing a semiconductor wafer in a semiconductor wafer manufacturing process; evaluating a manufactured semiconductor wafer; and subjecting a semiconductor wafer, which has been determined as an acceptable wafer by the evaluation, to preparation for shipping as a product semiconductor wafer; wherein the evaluation is performed by the above semiconductor wafer evaluation method.

Manufacturing method 3 includes evaluating, by the semiconductor wafer evaluation method according to an aspect of the present invention, a semiconductor wafer manufactured in a semiconductor wafer manufacturing process. Then, if as a result of the evaluation, the evaluated semiconductor wafer is determined as an acceptable wafer, this semiconductor wafer is subjected to the preparation for shipping as a product semiconductor wafer. On the other hand, if it is determined as an unacceptable wafer, it is not shipped as a product or it is subjected to the preparation for shipping as a product semiconductor wafer after being subjected to a process for removing or reducing abnormal substances. Thus, a high-quality silicon wafer can be stably supplied in which the introduction and/or adhesion of the abnormal substances onto the surface can be suppressed. The preparation for shipping as a product semiconductor wafer is as described above.

In Manufacturing method 3, whether an evaluated semiconductor wafer is an acceptable wafer or an unacceptable wafer can be determined on the basis of the standard of the acceptable level/unacceptable level regarding a semiconductor wafer described above. The standard, such as a threshold, for determining as an unacceptable wafer are not limited in particular, and can be set in accordance with the quality required for a product semiconductor wafer.

An embodiment of Manufacturing method 3 is a method of manufacturing a polished wafer. The detail of the method of manufacturing a polished wafer is as described above. However, Manufacturing method 3 is not limited to the method of manufacturing a polished wafer, and can be a method of manufacturing various types of semiconductor wafers, for example, those described above.

EXAMPLES

The present invention will be described in greater detail below through Examples. However, the present invention is not limited to the embodiments shown in Examples.

1. Preparation of a Semiconductor Wafer (Polished Wafer) to be Evaluated

A polished wafer was obtained by performing rough polishing (lapping), etching by an etchant, mirror polishing (finish polishing), and washing on a silicon wafer sliced from a silicon single crystal ingot grown by the Czochralski method.

2. Performance Evaluation of Light-Scattering Type Surface Inspection Apparatus

As a light-scattering type surface inspection apparatus, Surfscan series SP2 manufactured by KLA TENCOR Corporation was used, the minimum detection size was set to the minimum detection size 30 nm which can be processed by the analysis unit, a specific defect present on the surface of the polished wafer was repeatedly measured 100 times, and the standard deviation a of the detection variation of the detected defect size was calculated as σ=0.8 nm. The minimum detection size which can be processed by the analysis unit was set taking into consideration the surface quality (haze, the number of defects and the like) of a wafer to be evaluated.

3. Determination of Target Abnormal Substances Overlooking Rate

When a minimum detection size (X) is set to 35 nm in the analysis unit of the light-scattering type surface inspection apparatus, the probability for a defect having the defect size of 36 nm to be overlooked by the apparatus-induced overlooking in one time of inspection is calculated as follows.

Since X=35 nm, m=36 nm, and σ=0.8 nm for calculating Relational Expression 1 described above are established, Z=−1.25 is calculated. By substituting the calculated Z into Relational Expression 1, the apparatus-induced abnormal substances overlooking rate Φ is calculated as Φ=0.1056. This value was determined as the target abnormal substances overlooking rate.

4. Setting of Evaluation Standard

When the minimum detection size (X) is set to 35 nm in the analysis unit of the light-scattering type surface inspection apparatus, the minimum number of times of inspection A and the abnormal substances detection threshold B, in which the apparatus-specific abnormal substances overlooking rate "a" becomes equal to or less than 0.1056 which is the target abnormal substances overlooking rate, are obtained for the defect of each size by using Relational Expression 2. That is, a combination of the minimum "n" and "k" by which "a" becomes equal to or less than 0.1056 is obtained as n=A and k=B by Relational Expression 2. The results are shown in Table 1.

TABLE 1

In a case of the minimum detection size X = 35 nm and the target abnormal substances overlooking rate = 0.1056

| Defect size m (nm) | Number of times of inspection A (number of times) | Abnormal substances detection threshold B (number of times) |
| --- | --- | --- |
| 35 | 6 | 5 |
| 34 | 6 | 5 |
| 33 | 6 | 5 |
| 32 | 6 | 5 |
| 31 | 9 | 7 |

Furthermore, when the minimum detection size (X) is set to a value shown in Tables 2 to 6 in the analysis unit of the light-scattering type surface inspection apparatus, the probability for a defect having the defect size of 36 nm to be overlooked by apparatus-induced overlooking in one time of inspection was calculated in the same manner as the above Example. The value calculated in this manner was determined as the target abnormal substances overlooking rate, and the minimum number of times of inspection A and abnormal substances detection threshold B, in which the apparatus-specific abnormal substances overlooking rate "a" becomes equal to or less than the respective target abnormal substances overlooking rates, are obtained for the defect having the size "m" shown in Tables 2 to 6 by using Relational Expression 2. The results are shown in Tables 2 to 6.

TABLE 2

In a case of the minimum detection size X = 34 nm and the target abnormal substances overlooking rate = 0.0062

| Defect size m (nm) | Number of times of inspection A (number of times) | Abnormal substances detection threshold B (number of times) |
| --- | --- | --- |
| 35 | 6 | 5 |
| 34 | 6 | 5 |
| 33 | 6 | 5 |
| 32 | 8 | 7 |
| 31 | 16 | 11 |

TABLE 3

In a case of the minimum detection size X = 33 nm and the target abnormal substances overlooking rate = 8.84E−05

| Defect size m (nm) | Number of times of inspection A (number of times) | Abnormal substances detection threshold B (number of times) |
| --- | --- | --- |
| 35 | 6 | 5 |
| 34 | 6 | 5 |
| 33 | 6 | 5 |
| 32 | 10 | 8 |
| 31 | 28 | 18 |

TABLE 4

In a case of the minimum detection size X = 32 nm and the target abnormal substances overlooking rate = 2.87E−07

| Defect size m (nm) | Number of times of inspection A (number of times) | Abnormal substances detection threshold B (number of times) |
| --- | --- | --- |
| 35 | 6 | 5 |
| 34 | 6 | 5 |
| 33 | 6 | 5 |
| 32 | 14 | 10 |
| 31 | 51 | 32 |

TABLE 5

In a case of the minimum detection size X = 31 nm and the target abnormal substances overlooking rate = 2.05E−10

| Defect size m (nm) | Number of times of inspection A (number of times) | Abnormal substances detection threshold B (number of times) |
| --- | --- | --- |
| 35 | 6 | 5 |
| 34 | 6 | 5 |
| 33 | 10 | 8 |
| 32 | 21 | 15 |
| 31 | 72 | 44 |

TABLE 6

In a case of the minimum detection size X = 30 nm and
the target abnormal substances overlooking rate = 3.19E−14

| Defect size m (nm) | Number of times of inspection A (number of times) | Abnormal substances detection threshold B (number of times) |
|---|---|---|
| 35 | 6 | 5 |
| 34 | 9 | 7 |
| 33 | 14 | 10 |
| 32 | 23 | 15 |
| 31 | 95 | 57 |

The results shown in Tables 1 to 6 indicate that the apparatus-induced abnormal substances overlooking rate Φ calculated by Relational Expression 1 becomes higher for a defect having a smaller size, and that, therefore by increasing the number of times of inspection on the basis of the apparatus-specific abnormal substances overlooking rate "a" which also includes the probabilistic factor in addition to the apparatus-induced factor, the defect detection with an overlooking rate comparable to the target abnormal substances overlooking rate can be performed.

An aspect of the present invention is useful in the field of manufacturing various kinds of semiconductor wafers.

Although the present invention has been described in considerable detail with regard to certain versions thereof, other versions are possible, and alterations, permutations and equivalents of the version shown will become apparent to those skilled in the art upon a reading of the specification. Also, the various features of the versions herein can be combined in various ways to provide additional versions of the present invention. Furthermore, certain terminology has been used for the purposes of descriptive clarity, and not to limit the present invention. Therefore, any appended claims should not be limited to the description of the preferred versions contained herein and should include all such alterations, permutations, and equivalents as fall within the true spirit and scope of the present invention.

Having now fully described this invention, it will be understood to those of ordinary skill in the art that the methods of the present invention can be carried out with a wide and equivalent range of conditions, formulations, and other parameters without departing from the scope of the invention or any Examples thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method of setting an evaluation standard of a semiconductor wafer,
    wherein the evaluation standard is a standard that is used in evaluating a semiconductor wafer by a light-scattering type surface inspection apparatus which detects abnormal substances present on a surface of the semiconductor wafer as a light point defect;
    the light-scattering type surface inspection apparatus comprises an analysis unit which outputs, as abnormal substances data, only the data of abnormal substances detected as abnormal substances having a size equal to or greater than X, where X is a minimum detection size which is set in the analysis unit;
    setting the evaluation standard is setting the number of times of inspection A and an abnormal substances detection threshold B, in which the A and B are values to be used in an evaluation of determining a light point defect, at which abnormal substances data is output B or more times within A-times of inspection, as a light point defect brought by abnormal substances, where A is an integer equal to or greater than 2, and B is an integer equal to or greater than 1 and equal to or less than A; and
    the method comprises setting the A and B on the basis of an abnormal substances overlooking rate "a" specific to the light-scattering type surface inspection apparatus specified by an apparatus-induced abnormal substances overlooking rate Φ due to the light-scattering type surface inspection apparatus and a probabilistic abnormal substances overlooking rate, in which the apparatus-induced abnormal substances overlooking rate Φ is higher as the target abnormal substances size to be detected is smaller, and the probabilistic abnormal substances overlooking rate is lower as the number of times of inspection increases.

2. The method of setting an evaluation standard of a semiconductor wafer according to claim 1,
    wherein the apparatus-induced abnormal substances overlooking rate Φ is a probability for the light-scattering type surface inspection apparatus not to output, as abnormal substances data, data of abnormal substances having a size "m" present on a surface of a semiconductor wafer to be evaluated, in the analysis unit, and is obtained by Relational Expression 1 below, and the apparatus-specific abnormal substances overlooking rate "a" is obtained by Relational Expression 2 below;

(Relational Expression 1)
$$\phi(z) = \frac{1}{\sqrt{2\pi}} e^{-\frac{z^2}{2}}$$

$$\Phi(z) = \int_{-\infty}^{z} \phi(y) dy$$

wherein, in Relational Expression 1, $Z=(X-m)/\sigma$, and $\sigma$ is a standard deviation of a variation in detection size due to the light-scattering type surface inspection apparatus;

$$a = P(k) + P(k+1) + \ldots + P(n) \quad \text{(Relational Expression 2)}$$

wherein, in Relational Expression 2, P is a probability for abnormal substances present on a surface of a semiconductor wafer to be probabilistically overlooked k-times without being detected in n-times of inspection, where $k \leq n$, and is calculated by a binomial distribution below;

$$P[X=k] = \binom{n}{k} \Phi^k (1-\Phi)^{n-k} \text{ for } k = 0, 1, 2, \ldots, n$$

$$\binom{n}{k} = {}_nC_k = \frac{n!}{k!(n-k)!}.$$

3. The method of setting an evaluation standard of a semiconductor wafer according to claim 1, which comprises:
setting a target abnormal substances overlooking rate; and
setting the A and B to values such that the overlooking rate calculated from the A and B is equal to or lower than the target abnormal substances overlooking rate.

4. The method of setting an evaluation standard of a semiconductor wafer according to claim 3,
wherein the target abnormal substances overlooking rate is set to a lower value as a quality requested for a semiconductor wafer to be evaluated is higher.

5. A method of evaluating a semiconductor wafer,
which comprises:
setting evaluation standard by the method of setting an evaluation standard of a semiconductor wafer according to claim 1; and
evaluating a semiconductor wafer based on the evaluation standard that has been set.

6. A method of evaluating a semiconductor wafer manufacturing process,
which comprises evaluating, by the method of evaluating a semiconductor wafer according to claim 5, a semiconductor wafer manufactured in a semiconductor wafer manufacturing process to be evaluated; and
determining, on the basis of a result of the evaluating, necessity of a process control of the semiconductor wafer manufacturing process to be evaluated.

7. A method of manufacturing a semiconductor wafer,
which comprises:
manufacturing a semiconductor wafer in a semiconductor wafer manufacturing process;
evaluating at least one semiconductor wafer manufactured in the semiconductor wafer manufacturing process by the method of evaluating a semiconductor wafer according to claim 5;
determining, on the basis of a result of the evaluating, necessity of a process control of the semiconductor wafer manufacturing process; and,
when it is determined, as a result of the determining, that the process control is not required, then further manufacturing a semiconductor wafer in the semiconductor wafer manufacturing process without the process control, while when it is determined, as a result of the determining, that the process control is required, then further manufacturing a semiconductor wafer in the semiconductor wafer manufacturing process after performing the process control of the semiconductor wafer manufacturing process.

8. A method of manufacturing a semiconductor wafer,
which comprises:
preparing a semiconductor wafer lot including a plurality of semiconductor wafers;
extracting at least one semiconductor wafer from the semiconductor wafer lot;
evaluating the extracted semiconductor wafer by the method of evaluating a semiconductor wafer according to claim 5; and
subjecting at least one semiconductor wafer included in the same lot as a semiconductor wafer which has been determined as an acceptable wafer by the evaluating, to preparation for shipping as a product semiconductor wafer.

9. A method of manufacturing a semiconductor wafer,
which comprises:
manufacturing a semiconductor wafer in a semiconductor wafer manufacturing process;
evaluating a manufactured semiconductor wafer by the method of evaluating a semiconductor wafer according to claim 5; and
subjecting a semiconductor wafer which has been determined as an acceptable wafer by the evaluating, to preparation for shipping as a product semiconductor wafer.

* * * * *